(12) United States Patent
Zeng

(10) Patent No.: US 9,354,233 B2
(45) Date of Patent: May 31, 2016

(54) A+ BIOMARKER ASSAYS

(75) Inventor: Gang Zeng, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 954 days.

(21) Appl. No.: 13/141,525

(22) PCT Filed: Feb. 19, 2010

(86) PCT No.: PCT/US2010/024769
§ 371 (c)(1),
(2), (4) Date: Jun. 22, 2011

(87) PCT Pub. No.: WO2010/096674
PCT Pub. Date: Aug. 26, 2010

(65) Prior Publication Data
US 2011/0311998 A1    Dec. 22, 2011

Related U.S. Application Data

(60) Provisional application No. 61/153,991, filed on Feb. 20, 2009.

(51) Int. Cl.
*G01N 33/574* (2006.01)
*G01N 33/53* (2006.01)
*G01N 33/536* (2006.01)

(52) U.S. Cl.
CPC ........ *G01N 33/57434* (2013.01); *G01N 33/536* (2013.01)

(58) Field of Classification Search
CPC ............................. G01N 33/53; G01N 33/574
USPC .................................................. 435/7.23, 7.1
See application file for complete search history.

(56) References Cited

U.S. PATENT DOCUMENTS

2008/0254481 A1* 10/2008 Love et al. .................... 435/7.1

FOREIGN PATENT DOCUMENTS

| CN | 101344526 A | 1/2009 |
|---|---|---|
| WO | 2004029627 A1 | 4/2004 |

OTHER PUBLICATIONS

Sreekumar et al. (J Natl Cancer Inst 2004, 96: 834-43).*
Zeng et al. (Int. J. Cancer, 2005, 114: 268-273).*
Liu et al. (Journal of Data Science 2005, 3: 257-278).*
Xie et al. (Journal of Translational Medicine 2011, 9: 43).*
Sreekumar et al. (J Natl Cancer Inst, 2004, 96: 834-43).*
Steuber, T., et al. (2008) "Serum Markers for Prostate Cancer: A Rational Approach to the Literature" European Urology, 54:31-40.
Nilsson, B. et al. (2001) "Autoantibodies to Prostasomes as New Markers for Prostate Cancer" Uppsala Journal of Medical Science, 106:43-49.
Bradford, T. et al. (2006) "Cancer Immunomics: Using Autoantibody Signatures in the Early Detection of Prostate Cancer" Urologic Oncology: Seminars and Original Investigations, 24:237-242.
Wang, X. et al. (2005) "Autoantibody Signatures in Prostate Cancer" New England Journal of Medicine, 353:1224-1234.
Bensalah, K. et al. (2008) "New Circulating Biomarkers for Prostate Cancer" Prostate Cancer Prostatic Dis. 11:112-120.
International Search Report received in PCT/US2010/024769 mailed Nov. 4, 2010.
Chinese Office Action for Chinese Application No. 201080008503.3; mailed Jan. 20, 2014.
Office Action received in CN 201080008503.3, mailed Jul. 22, 2014.

\* cited by examiner

*Primary Examiner* — Yan Xiao
(74) *Attorney, Agent, or Firm* — Suzannah K. Sundby, Esq.; Canady + Lortz LLP

(57) ABSTRACT

Disclosed herein assay methods which comprise detecting the presence, absence or amount of at least one antibody which specifically binds a first biomarker or an epitope thereof and at least one second biomarker in a sample which comprises a single reaction step whereby both a first capture reagent for the antibody and a second capture reagent for the second biomarker are together contacted with the sample, and detecting the presence, absence or amount of the antibody, and detecting the presence, absence or amount of the second biomarker. Also disclosed are assay methods for prostate cancer.

13 Claims, 4 Drawing Sheets

Comparison of the A+PSA index with PSA in patients with prostate cancer vs. BPH

| Marker | Sensitivity | Specificity | Accuracy | AUC |
|---|---|---|---|---|
| PSA only | 65.00%(13/20) | 50.00% (8/16) | 58.33% | 0.6641 |
| A+ PSA | 75.00%(15/20) | 75.00%(12/16) | 75.00% | 0.8531 |

A+ BIOMARKER ASSAYS

CROSS-REFERENCE TO RELATED APPLICATIONS

This application claims the benefit of U.S. Patent Application Ser. No. 61/153,991, filed 20 Feb. 2009, which is herein incorporated by reference in its entirety.

ACKNOWLEDGEMENT OF GOVERNMENT SUPPORT

This invention was made with Government support under CA128086 and CA137651 awarded by the National Institutes of Health. The Government has certain rights in the invention.

REFERENCE TO A SEQUENCE LISTING SUBMITTED VIA EFS-WEB

The content of the ASCII text file of the sequence listing named "034044_072WO1_ST25" which is 3.89 kb in size was created on 19 Feb. 2010 and electronically submitted via EFS-Web herewith the application is incorporated herein by reference in its entirety.

BACKGROUND OF THE INVENTION

1. Field of the Invention

The present invention generally relates to antibody plus (A+) biomarker assays for detecting and diagnosing cancer in subjects.

2. Description of the Related Art

Molecular identification of tumor-associated antigens (TAAs) has clearly demonstrated that the human immune system can react with endogenously arising cancer cells. See van der Bruggen et al. (1991) Science 254:1643-7. Both the cellular and humoral arms of the human immune system recognize TAA derived from cancer cells. See Rosenberg S A (2001) Nature 411:380-4; and Old et al. (1998) J Exp Med 187:1163-7. Of particular interest to the serological analysis of human cancers is the identification of TAA recognized by antibodies (Ab) present in the sera of cancer patients. See Sahin et al. (1997) Curr Opin Immunol 9:709-16. Ab-defined TAA provide molecular details of the humoral immune response to autologous tumors.

To investigate Ab responses that cover a wide spectrum of patients with any particular cancer requires a large panel of TAA. Currently, two main strategies are used for profiling circulating Ab: (1) conventional serological surveys using phage lysates encoding specific TAA, and (2) ELISA-based approaches using purified recombinant proteins as the antigenic targets. See Stone et al. (2003) Int J Cancer 104:73-84; and Tan et al. (2005) N Engl J Med 353:2815-7. The former approach requires large amounts of sera individually preadsorbed with E. coli phage lysates for reduction of background; the latter is a robust method but requires the purification of proteins encoded by individual TAA. See Zhang et al. (2003) Cancer Epidemiol Biomarkers Prev 12:136-43; and Lagarkova et al. (2003) Immunol Lett 85:71-4.

SUMMARY OF THE INVENTION

The present invention provides assay methods for at least one antibody which specifically binds a first biomarker or an epitope thereof and at least one second biomarker in a sample which comprise a single reaction step whereby both a first capture reagent for the antibody and a second capture reagent for the second biomarker are together contacted with the sample, and detecting the presence, absence, or amount of the antibody, and detecting the presence, absence or amount of the second biomarker.

The assays of the present invention may be used for diagnosing or designating a subject as having an affliction or likely to have the affliction, which comprises diagnosing or designating the subject as having the affliction or likely to have the affliction where the combination of the presence, absence, or amount of the antibody with the presence, absence, or amount of the second biomarker is indicative of the affliction.

In some embodiments, the presence, absence, or amount of the antibody is assigned a first value and the presence, absence, or amount of the second biomarker is assigned a second value, and the first value and the second value are combined to give an index value, and then the index value is used to diagnose or designate the subject as having the affliction or likely to have the affliction. In some embodiments, the first value is assigned 0 for the absence of the antibody and 1 for the presence of the antibody; and the second value is assigned 0 for a normal amount of the second biomarker, 1 for an abnormally high amount of the second biomarker, or a number between 0 and 1 for an amount of the second biomarker which is between the normal amount and the abnormally high amount. In some embodiments, the sum of the first value and the second weighted value is equal to or greater than a given number, the subject is designated as having the affliction. In some embodiments, logistical regression analysis is used to calculate an index value based on the first value and the second value. In these embodiments, the subject is designated as having the affliction where the index value is equal or greater than a given number.

In some embodiments, the affliction is a cancer such as prostate cancer, liver cancer, breast cancer, lung cancer, ovarian cancer, pancreatic cancer, gastric cancer, thyroid cancer, urothelial cell carcinoma, and the like including other epithelial cancers known in the art.

In some embodiments where the cancer is prostate cancer, the first biomarker is a prostate cancer associated antigens such as NY-ESO-1, MAGE-1, XAGE-1b, SSX2,4, P53, MUC-1, CEA, SOX2, AMACR, p90 autoantigen, LEDGFp75, HIP-1, p62 autoantigen, GRP78, TMPRSS2-ERG fusion, and the like, and epitopes thereof and the second biomarker is prostate specific antigen. In some embodiments the epitopes are selected from the group consisting of: AMACR:341-371; p90:796-827; LEDGFp75:310-342; HIP-1:150-180; HIP-1:338-378; SSX2, 4:110-139; NY-ESO-1:1-40; XAGE-1b:1-25; and XAGE-1b:57-81. In some embodiments, one or more than one type of autoantibody is assayed, e.g. a panel of 6 different "first" biomarkers are used to detect and/or measure six different types of autoantibodies in conjunction with assaying at least one second biomarker.

In some embodiments, the first biomarker is a first tumor antigen and the second biomarker is a second tumor antigen. In some embodiments, the first tumor antigen and/or the second tumor antigen is a tumor marker which may be a tumor-specific antigen or a tumor-associated antigen. In some embodiments, the first tumor antigen and/or the second tumor antigen is a cancer-specific marker or a tissue-specific marker. In some embodiments, the second tumor antigen is selected from the group consisting of alpha fetal protein (AFP), cancer antigen 125 (CA-125), carcinoembryonic antigen (CEA), human epidermal growth factor receptor 2 (Her2/neu), tumor-associated antigen CA 15-3, tumor-associated antigen CA 19.9, human aspartyl (asparaginyl) beta-hydroxylase (HAAH), thyroglobulin, bladder tumor antigen, and the like. In some embodiments, the first tumor antigen is NY-ESO-1, XAGE-1b, or SSX2,4 and the second tumor antigen is prostate specific antigen (PSA), alpha fetal protein (AFP), cancer antigen 125 (CA-125), carcinoembryonic antigen (CEA), human epidermal growth factor receptor 2 (Her2/neu), tumor-associated antigen CA 15-3, tumor-associated antigen CA 19.9, human aspartyl (asparaginyl) beta-hydroxylase (HAAH), thyroglobulin, bladder tumor antigen, or the like. In some embodiments, the amount of more than one second tumor antigen may be assayed.

In some embodiments, the present invention provides a purified or isolated peptide selected from the group consisting of AMACR:341-371; p90:796-827; LEDGFp75:313-345; HIP-1:150-180; SSX2, 4:110-139; XAGE-1b:1-25; NY-ESO-1:1-40; XAGE-1b:57-81; AMACR:251-282; HIP-1:338-378; and p62:156-184.

In some embodiments, the present invention provides kits for conducting an assay according to the present invention which have the capture reagents for the first biomarker and the second biomarker packaged together. For example, a kit for conducting an autoAb+PSA assay comprises at least one capture reagent which specifically binds an autoAb against prostate cancer associated antigen (which is not prostate specific antigen) and at least one antibody which specifically binds PSA packaged together.

The assays of the present invention may be used for early detection (e.g. before an observable clinical symptom) of an affliction, such as cancer in a subject, determining whether a subject is likely to suffer a recurrent cancer, determining the prognosis of a subject suffering from a cancer (e.g. designating the subject as likely to have a favorable or less favorable recovery or response to certain treatment where the sum of the first value and the second value are above or below a given value).

In some embodiments, the present invention provides a method of diagnosing or designating a subject as having or likely to have prostate cancer, which comprises assaying a sample from the subject for the presence, absence or amount of an autoantibody which specifically binds a prostate cancer associated antigen or an epitope thereof, and for the presence, absence or amount of prostate specific antigen, wherein the prostate cancer associated antigen is not prostate specific antigen, and diagnosing or designating the subject as having or likely to have prostate cancer where the combination of the presence, absence, or amount of the autoantibody with the presence, absence, or amount of prostate specific antigen is indicative of prostate cancer. In some embodiments, assaying the sample is conducted in a single reaction step whereby both a first capture reagent for the autoantibody and a second capture reagent for prostate specific antigen are together contacted with the sample.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein.

DETAILED DESCRIPTION OF THE INVENTION

Figures 1A, 1B:
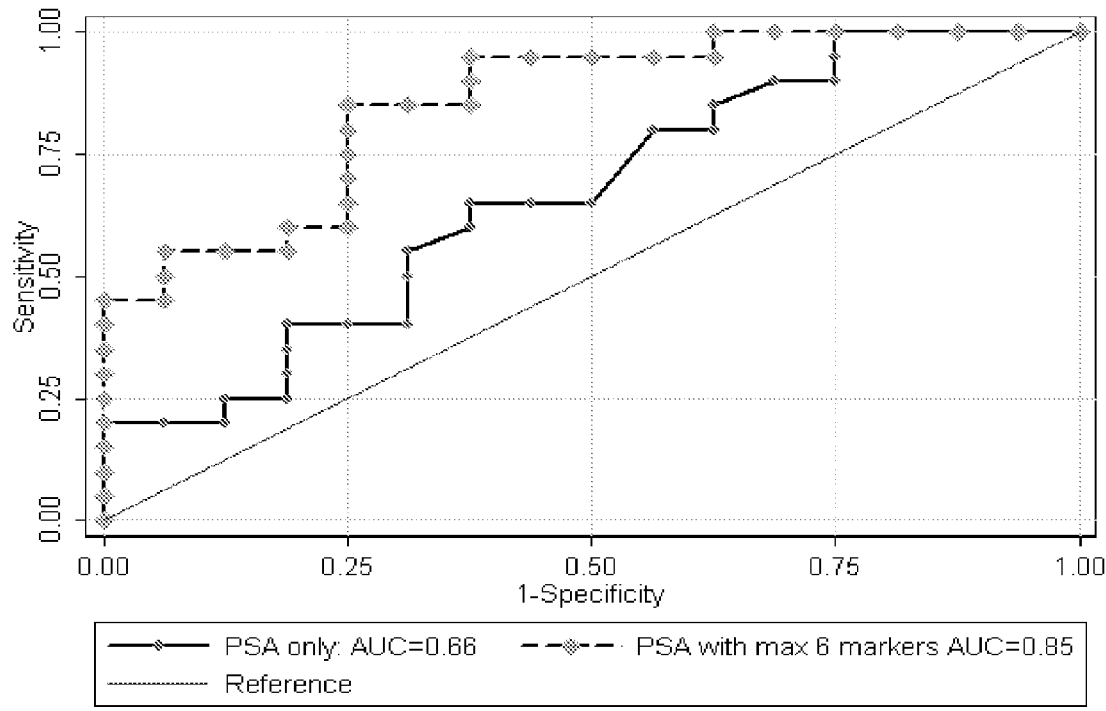
FIG. 1A shows the ROC curves from the PSA and autoAb+ PSA assays of 36 patients (20 with prostate cancer and 16 with BPH). PSA levels were determined using commercially available ELISA kit. The autoantibodies were measured against 6 peptide epitopes using ELISA.
FIG. 1B shows a table comparing the differentiation power between the combined index of an autoAb+PSA assay and PSA alone in the specified group of patients.

The present invention provides assays for diagnosing a subject as being at risk for a cancer or having the cancer wherein at least one autoantibody (autoAb) which specifically binds an epitope of a first TA plus at least one biomarker, such as the prostate cancer biomarker, prostate specific antigen (PSA), and are detected and/or measured in a sample obtained from the subject. In some embodiments, the autoantibody and the biomarker are detected or measured in the same sample. In some embodiments, the autoantibody and the biomarker are detected or measured in the same sample at the same time.

As used herein, an "epitope" is the part of a molecule that is recognized by a given antibody.

As used herein, "autoantibody" refers to an antibody produced by a subject that is directed against one or more of the subject's own antigens (e.g., a tumor antigen). As used herein, "antibody" refers to an immunoglobulin molecule and immunologically active portions thereof (i.e. molecules that contain an antigen binding site that specifically bind the molecule to which antibody is directed against). As such, the term antibody encompasses not only whole antibody molecules, but also antibody multimers and antibody fragments as well as variants (including derivatives) of antibodies, antibody multimers and antibody fragments. Examples of molecules which are described by the term "antibody" herein include, but are not limited to: single chain Fvs (scFvs), Fab fragments, Fab' fragments, F(ab')$_2$, disulfide linked Fvs (sdFvs), Fvs, and fragments comprising or alternatively consisting of, either a VL or a VH domain. The term "single chain Fv" or "scFv" as used herein refers to a polypeptide comprising a VH domain of antibody linked to a VL domain of an antibody. Antibodies of the invention may also include multimeric forms of antibodies. For example, antibodies of the invention may take the form of antibody dimers, trimers, or higher-order multimers of monomeric immunoglobulin molecules. The antibodies of the present invention can be natural or synthetic, polyclonal or monoclonal, or chimeric, and can be of any type (e.g. IgG, IgE, IgM, IgD, IgA and IgY), class (e.g. IgG$_1$, IgG$_2$, IgG$_3$, IgG$_4$, IgA$_1$ and IgA$_2$) or subclass of immunoglobulin molecule.

As used herein, a molecule, e.g. an antibody, that "specifically binds" another molecule, means that the interaction is dependent upon the presence of a specific structure, e.g. an epitope, on the molecule being bound. For example, an antibody which specifically binds a protein is recognizing and binding a specific structure on the protein rather than indiscriminate binding that gives rise to non-specific binding and/or background binding. As used herein, "non-specific binding" and "background binding" refer to an interaction that is not dependent on the presence of a specific structure (e.g. a particular epitope).

As used herein, a "biomarker" refers to a substance used as an indicator of a process, event, or condition. A biomarker can be a biomolecule such as a nucleic acid molecule (e.g. microRNA, genomic DNA, etc.), a protein, a polysaccharide, and the like. Biomarkers include tumor antigens and tumor markers.

As used herein, "tumor antigens" refer to tumor-specific antigens (TSAs), which generally classified as antigens present only on tumor cells and tumor-associated antigens (TAAs), which are generally classified as antigens present on some tumor cells and also some normal cells.

As used herein, a "tumor marker" is a substance that may be found in body tissues or bodily fluids that is produced by tumor cells or non-tumor cells in response to the presence of cancerous cells. Examples of tumor markers include AFP (in liver cancer), CA 125 (in ovarian cancer), CA 15-3 (in breast cancer), CEA (in ovarian, lung, breast, pancreas, and gastrointestinal tract cancers), and PSA (in prostate cancer). Tumor markers can be classified in two groups: cancer-specific markers and tissue-specific markers. Tumor markers include tumor antigens. However, tumor markers might not induce an immune response.

As used herein, a "subject suspected of having cancer" refers to a subject that presents one or more symptoms indicative of a cancer (e.g. a detectable lump or mass). A subject suspected of having cancer has generally not been tested for cancer. However, a subject suspected of having cancer may encompass one who has received an initial diagnosis (e.g. a CT scan or X-ray showing a mass) but for whom the type or stage of cancer is not known. A subject suspected of having cancer may also include one who once had cancer (e.g. individuals in remission). A subject suspected of having cancer may also be a subject at risk for cancer.

As used herein, a "subject at risk for cancer" refers to a subject with one or more risk factors for developing a specific cancer. Risk factors include genetic predisposition, environmental exposure, preexisting non-cancer diseases, previous cancers, and lifestyle.

As used herein, a "subject" is used interchangeably with "patient" and refers to a mammal such as a human.

As used herein, the "stage of cancer" refers to the level of advancement of a given cancer as is recognized by those skilled in the art. Criteria used to determine the stage of a cancer include, but are not limited to, the size of the tumor, whether the tumor has spread to other parts of the body and where the cancer has spread (e.g., within the same organ or region of the body or to another organ).

As used herein, "detecting the presence of cancer in a subject" refers to detecting the presence of a tumor antigen or autoantibody indicative of cancer.

As used herein, a "subject diagnosed with a cancer" refers to a subject having cancerous cells. The cancer may be diagnosed using any suitable method, including but not limited to, the diagnostic methods of the present invention.

The term "isolated" when used in relation to a nucleic acid molecule or a peptide or polypeptide refers to the given biomolecule that is separated from at least one component or contaminant with which it is ordinarily associated in nature.

As used herein, a "purified" composition refers to the removal of components (e.g. contaminants) from the composition.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like.

As used herein, a "capture reagent" refers to a molecule which is used to specifically bind an analyte of interest. The capture reagent may be immobilized on a substrate. For example, if the analyte of interest is an antigen, the capture reagent may be an antibody which specifically binds the antigen and if the analyte of interest is an antibody, then the capture reagent may be an epitope which the antibody specifically binds.

As used herein, an "A+ biomarker assay" or "A+B assay" refers to an assay of the present invention wherein at least one antibody (A) plus at least one biomarker (B) are detected and/or measured in a sample. As used herein, an "autoAb+ biomarker assay" or "autoAb+B assay" refers to an assay of the present invention wherein at least one autoantibody (autoAb) which specifically binds an epitope of a first biomarker plus at least one second biomarker (B) are detected and/or measured in a sample. As used herein, an "autoAb+TA assay" refers to an assay of the present invention wherein at least one autoantibody (autoAb) which specifically binds an epitope of a first biomarker plus at least one second biomarker which is a tumor antigen (TA) are detected and/or measured in a sample. As used herein, an "A+ antigen assay" refers to an assay of the present invention wherein at least one antibody (A) plus at least one antigen are detected and/or measured in a sample. A+ biomarker assays encompass A+ antigen assays, autoAb+biomarker assays, and autoAB+TA assays.

According to the A+ biomarker assays of the present invention, antibody indices against a first biomarker are obtained and then combined with the values of the second biomarker using logistic regression methods known in the art, in which the binary dependent variable is 1 for the presence of the given cancer, disease or infection and 0 for the absence of the given cancer, disease or infection and the independent variables are the given biomarker(s) and the total antibody indices. The analysis may be done using the SAS statistical library (version 8.2 or 9.1, SAS Institute, Cary, N.C.). Based on the fitted model, a predicted probability can then be computed for a given subject using the index value calculated from the subject's sample. In general, an individual will be classified positive if the predicted probability exceeds a cutoff value, for instance, 0.50. The optimal cutoff value can be determined from an ROC curve as discussed below. The diagnostic power of an index for an A+ biomarker assay for a given cancer, disease or infection may be studied by examining its ROC curve, which is a plot of the sensitivity versus 1-specificity as the cut-off value varies over its entire range. Using the ROC curve one can evaluate the sensitivity of an index for an A+ biomarker assay for any given specificity. In addition, one could determine the optimal cutoff value by locating the cross point where the ROC curve meets with the straight line connecting the upper-left corner and the lower-right corner of the unit box for the ROC plot. For a given cutoff value, confidence intervals for the sensitivity and specificity can be obtained using the normal theory method or the bootstrap method. Statistical significance tests may also be performed to compare the ROC curves using AUC or partial AUC.

In order to exemplify autoAb+biomarker assays of the present invention, various B cell epitopes from prostate cancer-associated antigens (PCAAs) were investigated for their potential to complement conventional prostate specific antigen (PSA) tests. As used herein, "conventional PSA tests" refer to those which are approved by the U.S. Food and Drug Administration as of the date of the instant invention. Such conventional PSA tests are false positive-prone (7 out of 10 men having suspicious PSA levels will not have prostate cancer) and false negative-prone (2.5 out of 10 men with prostate cancer have no elevation in PSA). See Thompson et al. (2004) N Engl J Med 350(22):2239-46, which is herein incorporated by reference.

As disclosed herein, candidate peptides of potential B cell epitopes of AMACR, p90 autoantigen, LEDGFp75, HIP-1, SSX2,4, NY-ESO-1, and XAGE-1b, were predicted using methods known in the art. See PredictProtein: Rost et al. (2004) The PredictProtein Server. Nucleic Acids Research 32(Web Server issue):W321-W326; Zeng et al. (2005) Int J Cancer 114:268-73, and U.S. Pat. No. 7,420,032, which are herein incorporated by reference.

The sequences of AMACR, p90 autoantigen, LEDGFp75, HIP-1, SSX2,4, NY-ESO-1, and XAGE-1b, as identified by their GenBank accession and version GI numbers, are all herein incorporated by reference in their entirety, and are as follows:

AMACR=AAD10205.1, GI:4204097, sequence as pending on Nov. 30, 2009 p90 autoantigen=NP_065941.2, GI:190194355, sequence as pending on Jan. 17, 2010

LEDGFp75=AAC25167.1, GI:3283352, sequence as pending on Nov. 30, 2009

HIP-1=NP_005329.3, GI:38045919, sequence as pending on Feb. 7, 2010

SSX2,4=CAD90570.1, GI:30519359, sequence as pending on Oct. 15, 2008

NY-ESO-1=CAA05908.1, GI:3255991, sequence as pending on Oct. 11, 2008

XAGE-1b=CAC38108.1, GI:13992558, sequence as pending on Nov. 15, 2006

With respect to the sequences identified by the accession numbers above, the dates provided therewith indicate the date of the last update. It should be noted that when a sequence has been modified, it is given a new GenBank accession version number and a GI number. The revision history may be obtained through the internet based NCBI GenBank database (e.g. the WorldWideWeb at ncbi.nlm.nih.gov/sviewer/girevhist.cgi?). Thus, the indicated dates do not indicate that prior to the indicated date that the sequence was different to the one as pending on the given date. For example, for GI:190194355, the sequence is the same from Jun. 12, 2008 to Jan. 17, 2010, however, prior to Jun. 12, 2008, the sequence was different and was published as GI:24308239. Thus, as set forth herein:

```
AMACR:
                                              (SEQ ID NO: 1)
341-371 = KRDPFIGEHTEEILEEFGFSREEIYQLNSDK;

p90:
                                              (SEQ ID NO: 2)
796-827 = DREHKLANLHQKTKVQEEKIKTLQKEREDKEE;

LEDGFp75:
                                              (SEQ ID NO: 3)
313-345 = DRKRKQEEQMETEQQNKDEGKKPEVKKVEKKRE;

HIP-1:
                                              (SEQ ID NO: 4)
150-180 = MEYHTKNPRFPGNLQMSDRQLDEAGESDVNN;

SSX2,4:
                                              (SEQ ID NO: 5)
110-139 = KIMPKKPAEEGNDSEEVPEASGPQNDGKEL;

XAGE-1b:
                                              (SEQ ID NO: 6)
1-25 = MESPKKKNQQLKVGILHLGSRQKKI;

NY-ESO-1:
                                              (SEQ ID NO: 7)
1-40 = MQAEGRGTGGSTGDADGPGGPGIPDGPGGNAGGPGEAGAT;

XAGE-1b:
                                              (SEQ ID NO: 8)
57-81 = GVKVKIIPKEEHCKMPEAGEEQPQV;

AMACR:
                                              (SEQ ID NO: 9)
251-282 = KSDELPNQMSMDDWPEMKKKFADVFAKKTKAE;

HIP-1:
                                              (SEQ ID NO: 10)
338-378 = SQQNLFDNKFDDIFGSSFSSDPFNFNSQNGVNKDEKDHL
IE;
and p62:
                                              (SEQ ID NO: 11)
156-184 = DEEVSSPSPPQRAQRGDHSSREQGHAPGG.
```

The candidate peptides were then synthesized using methods known in the art. In particular, the candidate peptides were made using solid-phase synthesis on a peptide synthesizer (Gilson Co. Inc., Worthington, Ohio) at Genscript, Inc. (New Brunswick, N.J.) and GeneMed Synthesis, Inc. (San Antonio, Tex.). The molecular weight of each candidate peptide was evaluated by mass spectrometry to confirm its identity. The candidate peptides were re-suspended in DMSO solution at 20 mg/ml and stored at −20° C. until use.

The candidate peptides were then screened with serum samples from subjects having histologically confirmed prostate cancer and healthy subjects using methods known in the art. See Zeng et al. (2005) Int J Cancer 114:268-73; and Zeng et al. (2000) J Immunol 165:1153-9, which are herein incorporated by reference in their entirety. All serum samples were collected under UCLA approved IRB protocols. The subjects having histologically confirmed prostate cancer were in various clinical stages of cancer. Serum samples were stored at −20° C. until use. 10 ng/well of peptide was diluted in 50 µl PBS onto a 96-well MaxiSorp plate (Nunc, Denmark) overnight at 4° C. Control plates were coated with a peptide from β-galactosidase. All serum samples were diluted at 1:25, 1:125, and 1:625 with PBST (PBS buffer plus tween-20) containing 5% fetal bovine serum unless otherwise specified. Each sample at each of the three dilutions was loaded onto pre-coated ELISA plates. After a 2-hour incubation at room temperature, the plates were washed, and loaded with secondary antibodies (goat anti-human immunoglobulin conjugated with horseradish peroxidase, Sigma Co., St. Louis, Mo.) diluted with 5% fetal bovine serum in PBST. The plates were developed and absorbance at 450 nm was read by using an ELISA reader. The cut-off value was defined as the mean optimal density (OD) value plus 3 times standard deviations (SD) of healthy donors. OD values which exceeded the cut-off at 2 of the 3 dilutions of a serum sample from a cancer patient was regarded as positive.

The candidate peptides which were predicted and synthesized are set forth in Table 1 as follows:

TABLE 1

| Full-length PCAA Candidate Peptides | Frequency of recognition by healthy donors | Frequency of recognition by prostate cancer vs non-malignant prostate diseases* |
|---|---|---|
| AMACR | | |
| AMACR: 341-371 | 0/12 (012207), 0/12 (022207), 0/12 (031507), 0/14 (032007) | 2/20 vs 0/16 (012207), 2/20 vs 0/16(022207) |
| AMACR: 251-282 | | 0/16 (012007), 3/31 vs 2/29 (031507), 5/22 vs 5/35 (031707), 6/22 vs 6/35 (032007) |
| AMACR: 303-326 | 0/8 (012007) | 1/16 (012007) |
| AMACR: 199-214 | 0/8 (012007), 0/12 (022207) | 0/20 vs 0/16 (022207) |
| P90 | | |
| p90: 753-785 | 0/12 (031507) | 1/31 vs 0/29 (031507) |
| p90: 796-827 | 0/12 (031507), 0/12 (031707), 0/14 (031707) | 6/31 vs 2/29 (031507), 2/22 vs 3/35 (031707) |
| p90: 396-415 | | |
| p90: 556-576 | 0/8 (012007), 0/12 (022207), 0/14 (032007) | 2/16 (012007), 2/20 vs 1/16 (022207), 1/22 vs 1/35 (032007) |
| P62 | | |
| P62: 155-183 | | |
| P62: 214-251 | 0/12 (012207) | 0/20 vs 0/16 (012207), 0/15 (021207) |
| P62: 448-468 | | |
| LEDGFp75 | | |
| LEDGFp75: 222-252 | | |
| LEDGFp75: 313-345 | 1/12 (012207), 0/12 (021207), 0/12 (022207), 0/14 (032007) | 3/20 vs 0/16 (012207), 5/15 (021207), 1/20 vs 0/16 (022207), 1/22 vs 8/35 (032007) |
| LEDGFp75: 448-477 | 1/12 (031507), 1/14 (031707), 0/14 (032107) | 6/31 vs 4/29 (031507), 0/22 vs 8/35(031707), 2/22 vs 9/35 (032107) |
| LEDGFp75: 270-295 | | |
| LEDGFp75: 484-514 | | |
| HIP | | |
| HIP-1: 150-180 | 1/8 (012507), 0/12 (022207), 0/14 (031707) | 2/16 (012507), 2/20 vs 4/16 (022207), 4/22 vs 3/35 (031707) |
| HIP-1: 338-375 | 0/8 (012507) | 3/16 (012507) |
| HIP-1: 507-541 | 0/8 (012507), 0/12 (022207) | 2/16 (012507), 0/20 vs 0/16 (022207) |
| HIP-1: 845-867 | | |
| FLJ | | |
| FLJ: 14-31 | 0/8 (032207) | 0/13 vs 1/11 (032207) |
| VAMP3 | | |
| VA: 1-21 | 0/8 (032207) | 0/13 vs 2/11 (032207) |
| VA: 27-49 | 0/8 (032207) | 0/13 vs 1/11 (032207) |
| VA: 54-75 | 0/8 (041307) | 1/16 vs 0/16 (041307) |
| CyclinB1 | | |
| CY: 32-55 | 0/8 (032207) | 0/13 vs 3/11 (032207) |
| CY: 62-85 | 0/8 (032207) | 1/13 vs 2/11 (032207) |
| CY: 95-108 | 0/8 (032207) | 0/13 vs 2/11 (032207) |

TABLE 1-continued

| Full-length PCAA Candidate Peptides | Frequency of recognition by healthy donors | Frequency of recognition by prostate cancer vs non-malignant prostate diseases* |
|---|---|---|
| SSX2,4 | | |
| SSX2,4: 133-162 | 0/8 (112007) | 0/20 (112007) |
| SSX2,4: 110-139 | 0/8 (112007) | 2/20 (112007) |

*Positive recognition is defined as follows: Specific OD, or OD against the target peptide minus OD against a control peptide, is calculated. If specific OD for a given serum sample calculated under 3 different dilutions all exceeds the 95% cut-off (average OD from healthy donors + 2 SD), the sample is called positive. If specific OD for a given serum sample exceed 95% in 1 of the 3 dilution and 99% cut-off (average OD from healthy donors + 3 SD) in 1 of the 3 dilution, the sample is called positive.

A candidate peptide was confirmed as an epitope by validating that a serum sample positive against the given candidate peptide indeed reacts with its corresponding full-length PCAA. Specifically, the corresponding full-length PCAA was recombinantly expressed and Western blots were conducted using seropositive and seronegative serum samples according to methods known in the art. See e.g. Zeng et al. (2000) J Immunol 165:1153-9, which is herein incorporated by reference in its entirety. All the candidate peptides of Table 1 were subject to confirmation screening and those which did not confer recognition between autoantibodies of a subject suffering from prostate cancer and a healthy subject were not investigated further.

In addition to the ESO and XAGE peptides, confirmed epitopes which were used in the autoAb+PSA assay as exemplified herein are set forth in Table 2 as follows:

TABLE 2

| Confirmed Epitopes (Corresponding Full-length PCAA) | Frequency of recognition by healthy donors* | Frequency of recognition by prostate cancer patients* |
|---|---|---|
| AMACR: 341-371 (AMACR, GI:4204097) | 0/12 (012207), 0/12 (022207), 0/12 (031507) | 2/20 (012207), 2/20 (022207), 3/31 (031507) Recognized by about 10% patients |
| p90: 796-827 (P90, GI:190194355) | 0/12 (031507), 0/12 (031707), 0/14 (031707) | 6/31 (031507), 2/22 (031707) Recognized by 10-20% patients |
| LEDGFp75: 310-342 (LEDGFp75, GI:3283352) | 1/12 (012207), 0/12 (021207), 0/12 (022207), 0/14 (032007) | 3/20 (012207), 5/15 (021207), 1/20 (022207), 1/22 (032007) Recognized by 5-15% patients |
| HIP-1: 150-180 (HIP-1, GI:38045919) | 1/8 (012507), 0/12 (022207), 0/14 (031707) | 2/16 (012507), 2/20 (022207), 4/22 (031707) Recognized by 10-20% patients |
| HIP-1: 338-375 (HIP-1, GI:38045919) | 0/8 (012507) | 3/16 (012507) Recognized by 10-20% patients |
| SSX2,4: 110-139 (SSX2,4, GI:30519359) | 0/8 (112007) | 2/20 (112007) |

*Positive recognition is defined as follows: Specific OD, or OD against the target peptide minus OD against a control peptide, is calculated. If specific OD for a given serum sample calculated under 3 different dilutions all exceeds the 95% cut-off (average OD from healthy donors + 2 SD), the sample is called positive. If specific OD for a given serum sample exceed 95% in 1 of the 3 dilution and 99% cut-off (average OD from healthy donors + 3 SD) in 1 of the 3 dilution, the sample is called positive.

As set forth herein, the numerical range indicated after the colons of a name of a given peptide indicate the amino acid residues of the corresponding full length protein of which the given peptide consists. For example, for AMACR:341-371, the corresponding full length protein is GI:4204097. Thus, AMACR:341-371 consists of amino acid residues 341 to 371 of GI:4204097.

XAGE-1b:1-25, XAGE-1b:57-87, and NY-ESO-1:1-40 are previously confirmed epitopes. See e.g. U.S. Pat. No. 7,420,032, which is herein incorporated by reference. Out of these 3 previously confirmed epitopes and the 6 confirmed epitopes of Table 2, AMACR:341-371, LEDGFp75:313-345, SSX2, 4:110-139, p90:796-827, NY-ESO-1:1-40 and XAGE-1b:1-25 were randomly selected to determine whether assaying autoantibodies against such in combination with PSA levels could be used to differentiate serum samples from healthy subjects, subjects suffering from prostate cancer, and subjects having benign prostate hyperplasia (BPH).

Using ELISA based measurements, a combined autoAb+PSA index was created as the predicted probability of prostate cancer based on the logistic regression model. Specifically, the epitope indices of the epitopes were combined with the PSA values using a logistic regression method, in which the binary dependent variable is 1 for prostate cancer and 0 for BPH and the independent variables are PSA and the six epitope indices. For antibodies against a given epitope, an index value was calculated as the maximum of three normalized OD values from three different dilutions. For a given dilution, a normalized OD value was defined as (OD−mean OD of healthy subjects)/(SD of OD of healthy subjects).

Note that the index would exceed a cutoff value (thus classifying a subject as suffering from prostate cancer) if and only if at least one of the three normalized OD values exceeds the cutoff. The use of three dilutions instead of a single one is intended to catch potential variations in normalized OD values between different concentrations of serum samples. Receiver operating characteristic (ROC) curves were used to compare the diagnostic power between PSA levels and the combined PSA index for distinguishing a prostate cancer patient from a BPH patient.

Preliminary immunoassays using serum samples from 16 subjects having BPH and 20 subjects suffering from biopsy-confirmed prostate cancer evidenced that detection of PSA levels in combination with detection of autoantibodies against the panel of epitopes provides at least about a 23% increase in sensitivity, at least about a 50% increase in specificity, and at least a 29% increase in accuracy of distinguishing whether a subject has BPH or is suffering from prostate cancer. The results of the preliminary immunoassays are summarized in FIG. 1A and FIG. 1B. FIG. 1A depicts the ROC curves of PSA and autoAb+PSA and shows that the combined autoAb+PSA index has clearly better power than PSA alone for discriminating between prostate cancer and BPH. As shown in FIG. 1A, the area under the ROC curve (AUC) has also been increased substantially from 0.66 to about 0.85. FIG. 1B summarizes the sensitivity, specificity, and prediction accuracy with 0.50 being the cutoff for the predicted probability. Therefore, the autoAb+TA assays according to the present invention may be used to diagnose a subject as having benign tissue-plasia such as BPH or suffering from a cancer such as prostate cancer.

For example, to determine whether a subject should be classified as healthy (does not have prostate cancer), having BPH or having prostate cancer, a serum sample is obtained from the subject and then the amounts of autoantibodies plus the amount of PSA are assayed. Each autoantibody detected is given a value of 0 or 1. A value of 1 is assigned where the amount detected exceeds the cutoff value for the given autoantibody. The cutoff value for a given autoantibody is the average amount of the given autoantibody in healthy subjects plus two SD. For example, the average amount of autoantibody X in a pool of healthy subjects is 0.23 with a SD of 0.08. The cutoff value is 0.39. Thus, a value greater than 0.39 is assigned a value of 1 for autoantibody X. Then the sum of the autoantibody values are divided by the number of the autoantibodies detected to give a total autoantibody value. For example, if the sum of 6 autoantibody values total 4, the total autoantibody value is 0.67 (4/6). Then the amount of the PSA is detected and assigned a value from 0 to 1. For example, amounts below 4.0 ng/ml may be assigned a value of 0 and amounts above 10.0 ng/ml may be assigned a value of 1. In some embodiments, the value assigned may given a value of 0.5 for PSA at 4-10 ng/ml.

The total autoantibody value of a given sample is then added to the PSA value to give an index. If the index falls within a range consistent with that obtained from healthy subjects, the subject is classified as healthy. If the index falls within a range consistent with that obtained from subjects having BPH, the subject is classified as having BPH. If the index falls within a range consistent with that of subjects having prostate cancer, the subject is classified as having prostate cancer.

For example, in the ELISA based assays as exemplified herein, PSA amounts below 4.0 ng/ml were assigned a value of 0, PSA amounts above 10.0 ng/ml were assigned a value of 1, PSA amounts anywhere between 4-10 ng/ml were assigned a value of 0.5 and autoantibodies against AMACR:341-371, LEDGFp75:313-345, p62:155-375, p90:796-827, NY-ESO-1:1-40 and XAGE-1b:1-25 were detected. A subject was designated as having prostate cancer where the index was 1.5 or more.

The autoAb+TA assays of the present invention require the detection of at least one autoantibody against a first antigen plus a second antigen. Immunoassays known in the art either detect and measure (a) an antigen with an antibody as a capture reagent or (b) an antibody with an antigen as the capture reagent. No prior art immunoassay is known to comprise the detection and/or measurement of an antigen and an antibody at the same time in the same test sample as the measurement of an antibody is fundamentally different from the measurement of an antigen.

Therefore, to determine whether it is possible to detect and/or measure at least one autoantibody and at least one antigen in a single sample at the same time the following multi-analyte profiling bead-based assays (MAP assays), e.g. xMAP® technology (Luminex Corporation, Austin, Tex.) based bioassays, were conducted.

The capture reagents, i.e. the 6 epitopes and the anti-PSA antibody (MP011, Fullmoon Biosystems Inc., Sunnyvale, Calif.), were immobilized on microbeads, i.e. SeroMAP™ microspheres (Luminex Corporation, Austin, Tex.), using methods known in the art. Specifically, for each capture reagent, about 100 µl ($1.25 \times 10^6$ SeroMAP™ microspheres) of the stock microsphere suspension was pelleted by centrifugation at 10,000 rpm for 2 min. The supernatant was removed and the microspheres were resuspended in 25 µl PBS (pH 7.2) using vortex and sonication. This washing step was repeated and the microspheres were finally resuspended in 20 µl PBS. About 2.5 µl N-hydroxysulfosuccinimide (Sulfo-NHS, 50 mg/ml) and 2.5 µl 1-ethyl-3-(3-dimethylaminopropyl) carbodiimide hydrochloride (EDC, 50 mg/ml) were added to the microsphere suspension and gently mixed. The suspension was then incubated for 20 min at room temperature with vortex and sonication at 5 min intervals. The activated microspheres were then washed twice with 62 µl MES buffer (0.1 M, pH 6.0) and resuspended in 25 µl MES. 31.25 µg of the capture reagent (20 µg/µl in DMSO) diluted in 100 µl MES was then added to the activated and washed microspheres. The suspension was stirred for 2 hours with vortex and sonication at 30 min intervals. The capture reagent-conjugated microspheres were then washed and resuspended in PBS.

Similar to ELISA-based assays, the specific mean fluorescence intensity (MFI) ratio, i.e. the ratio of the MFI against the target peptide (epitope) to the MFI against a control peptide, was calculated. If the specific MFI ratios for a given serum sample under 3 different dilutions all exceeded the 95% cutoff (average MFI ratio from healthy subjects+2SD), the sample was considered to be positive. If the specific MFI ratio for a given serum sample exceeded the 95% cutoff in 1 of the 3 dilutions and the 99% cutoff (average MFI ratio from healthy subjects+3SD) in at least 1 of the other 2 dilutions, the sample was also defined as positive. The MAP assays exhibited improved signal to noise ratios over ELISA based assays in measuring autoantibodies (data not shown).

In particular, using MAP based measurements, a combined autoAb+PSA index was created as the predicted probability of prostate cancer based on the logistic regression model. Specifically, the autoantibody indices were combined with the PSA values using a logistic regression method, in which the binary dependent variable is 1 for prostate cancer and 0 for BPH and the independent variables are PSA and the six epitope indices. For antibodies against a given epitope, an index value was calculated as the mean of three normalized MFI (mean fluorescent intensity) values from three different dilutions. For a given dilution, a normalized MFI value was defined as (MFI−mean MFI of healthy subjects)/(SD of MFI of healthy subjects). For example, for patient X, if the MFI for autoantibodies against NY-ESO-1 at 1/10 serum dilution was 24.5 while the MFI against a control peptide, e.g. beta-galactosidase, is 0.94 at 1/10. A group of healthy subjects for example 12 of them were also determined at the same experiment. The mean MFI ratio for autoantibodies against NY-ESO-1 to control was 1.1 with a SD of 2.1. The normalized MFI ratio of autoantibodies against NY-ESO-1 for patient X at 1/10 dilution was (24.5/0.94−1.1)/2.1=11.9. Similarly, MFI ratio of autoantibodies against NY-ESO-1 at 1/20 and 1/50 serum dilutions were calculated, say 10.5 at 1/20 and 9.9 at 1/50. The mean of 3 normalized MFI would be (11.9+10.5+9.9)/3=10.8.

In these MAP based assays, to get the index for a given autoantibody, a logistic regression based on the MFI ratios as described above was calculated by linear regression (i.e. y=1/(1+exp(−linear regression)). The y, which is dichotomized variable (1=affliction, e.g. cancer; 0=normal, e.g. BPH/prostitis), is calculated from the coefficient of linear regression where the coefficients of the biomarkers were estimated from the data. The index values for each autoantibody may be combined to give a combined autoantibody index which is then considered with the PSA index to give a total index. If the total index obtained for a patient exceeds that as determined from healthy subjects, then the patient is considered to have the given affliction, e.g. prostate cancer.

Alternatively, as exemplified herein, to get the total index value for an autoAb+PSA assay, a logistic regression based on the MFI ratios as described above was calculated from the coefficient of linear regression where the coefficients of biomarkers were estimated from the training data such as the MFI ratios from the 124 healthy donors, the 121 BPH/prostatitis patients (non-cancer=0), and the prostate cancer patients (cancer=1). The probability (p) that a patient had prostate cancer was calculated as follows, where βn is the coefficient of linear regression between an autoantibody or biomarker and MFI is the ratio of that marker over a control. $\text{Log}(p/1-p)=\beta_0+\beta_1 \times mFI_1+\beta_2 \times mFI_2+\beta_3 \times mFI_3 \ldots \beta_n \times mFI_n$. Persons skilled in the art can readily make this calculation.

Thus, according to the MAP based autoAb+PSA assays described herein, if the p was smaller than 0.5, the subject was designated as healthy; 0.5 or larger, the subject is designated as having prostate cancer or likely to have prostate cancer.

It is noted that the average amount of a given biomarker for a pool of healthy subjects or the cutoff value need not be determined each time one desires to run an A+ biomarker assay on an unknown sample or subject. In other words, the index for a biomarker obtained from a subject may be determined by correlating the measured amount (μg/L) of the biomarker to previously determined index values obtained for given amounts, i.e. using a standardized table setting forth index values for a range of measured amounts.

Additionally, it should be noted that the coefficient of a biomarker(s) need not be determined each time one desires to run an A+ biomarker assay on an unknown sample or subject. In particular, a given coefficient need only be determined once for a given population group and that coefficient may be used as a standard coefficient. It is also noted that the coefficient of a given biomarker may vary between different population groups, e.g. different age groups, different ethnic groups, etc. Nevertheless, one skilled in the art may readily determine a biomarker coefficient for a given population group using the methods as described herein. Thus, it is contemplated that the A+ biomarker assays of the present invention may be fine tuned for a particular population group of interest. For example, one may readily determine the biomarker coefficients for a narrow population group, e.g. 50-55 year old males, using the methods disclosed herein in order to fine tune (e.g. increase the sensitivity, specificity, accuracy and ROC curve) the autoAb+PSA assay for male subjects who are between the ages of 50 to 55 years.

Figure 2:
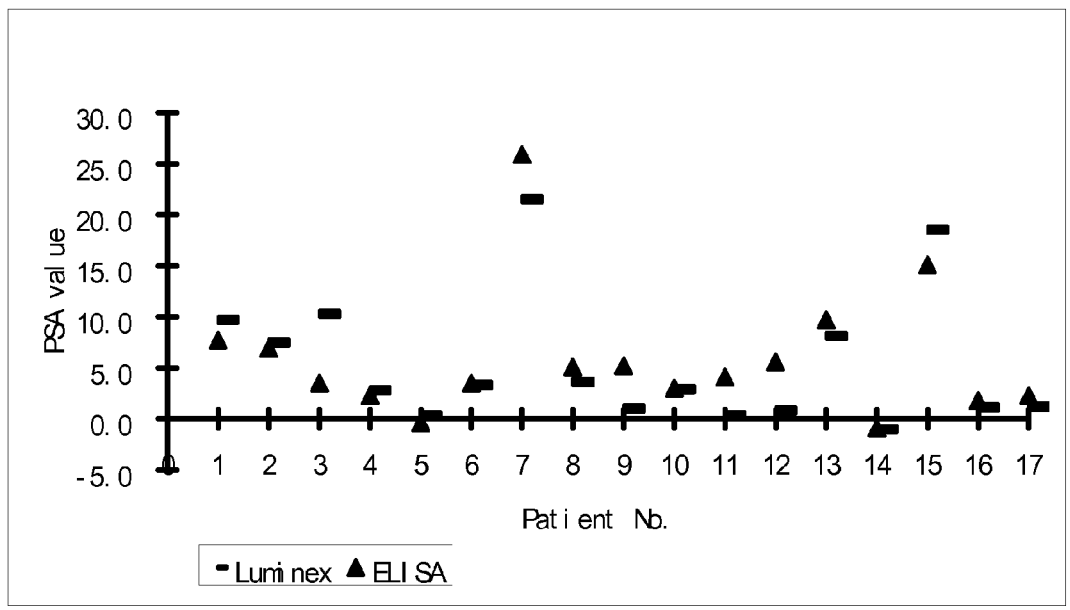
FIG. 2 is a graph comparing the PSA levels (ng/ml) in serum of randomly chosen subjects including healthy subjects, subjects having BPH, and subjects suffering from biopsy confirmed prostate cancer determined using ELISA based assays and MAP assays. The measured PSA levels, which ranged from 0.1 to 25 ng/ml, were determined to be similar when using MAP assays and commercially available ELISA based assays.

MAP assays for quantifying total PSA in serum were compared with traditional ELISA based assays. In these experiments, purified PSA standard (n=8) were used and were determined by MAP assays against observed fluorescence output (MFI) to produce a highly robust sigmoidal trendline with a correlation coefficient exceeding 0.95 (n=8). The results shown in FIG. 2 evidence that MAP assays may be used to quantify the total PSA levels in serum samples.

Figure 3:
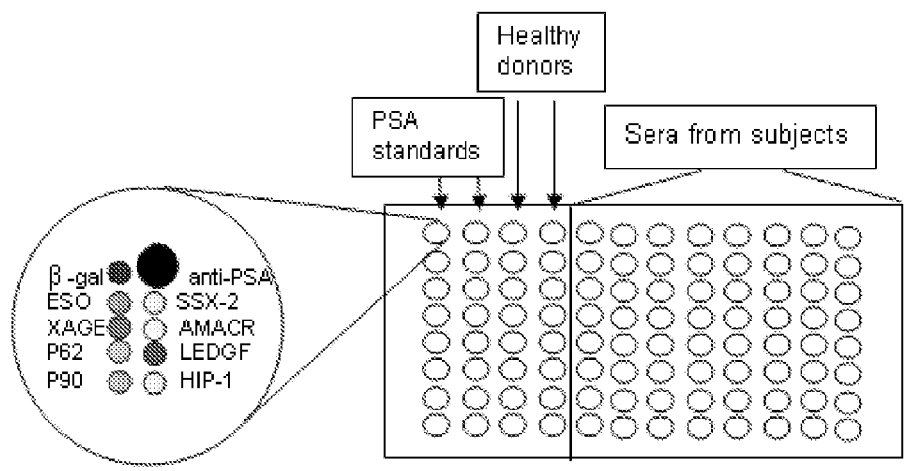
FIG. 3 is an illustration of an autoAb+PSA assay plate. Specifically, a 96-well plate (Millipore) for a MAP based assay is illustrated. An enlarged well shows 10 differently colored assay beads, 1 coated with control β-gal peptide, 8 coated with individual PCAA peptide for measuring autoantibodies, and 1 coated with anti-PSA antibody for measuring PSA. PSA standards (n=8) and sera from healthy donors (n=8) are each loaded in duplicates for the purpose of defining PSA units and seropositivity, respectively. A known positive serum against a given epitope or protein, e.g. NY-ESO-1, can be used as control. The shading and sizes of the beads are for demonstration only.
Figure 4A:
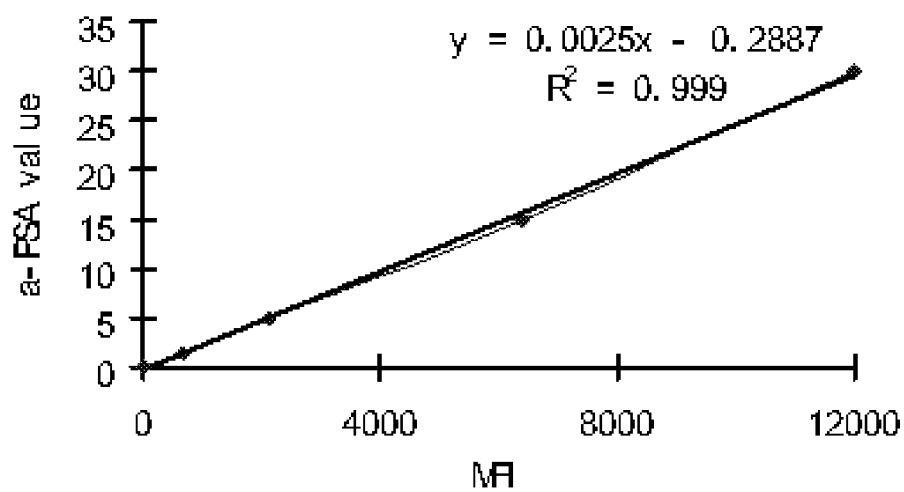
FIG. 4A graphically shows the comparison of the linear range for determining total PSA levels using a MAP based assay alone, in the absence of autoantibody detection. The linear regression equation is shown on top of the figure. Linear range was similarly achieved from 0-30 ng/ml total PSA in the presence of autoantibody detection against 8 epitopes as shown in FIG. 4B.
Figure 4B:
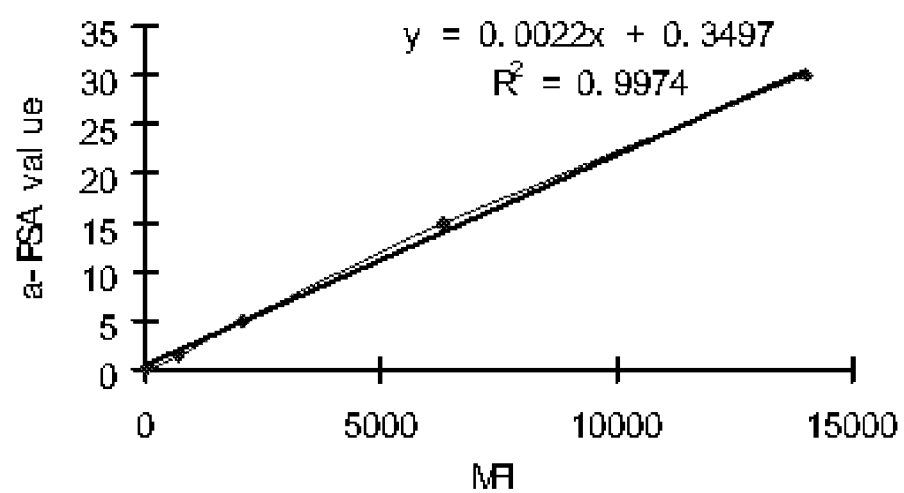
FIG. 4B graphically shows the comparison of the linear range for determining total PSA levels using the MAP based autoAb+PSA multiplex assay (i.e. PSA levels when measured in the same sample from the same reaction step as autoantibodies against 8 peptide epitopes). The linear regression equation is shown on top of the figure.

Specifically, the PSA levels in serum samples of known PSA levels (measured using commercially available PSA kits) ranging from 500 pg/ml to as high as 5 μg/ml were quantified using the MAP assay configuration schematically shown in FIG. 3. As shown in FIGS. 4A and 4B, the measured PSA levels from MAP assays where PSA levels were measured alone or in combination with a plurality of autoantibodies were substantially similar as well as consistent with the known PSA levels from ELISA based assays. These results evidence that assaying an antigen and one or more antibodies from the same reaction step in the same sample does not significantly effect the measurement of a given analyte. Thus, at least one antibody and at least one antigen may be assayed in the same sample from the same reaction step.

Therefore, the present invention provides A+ biomarker multiplex assays. As used herein, an "A+ biomarker multiplex assay" and "A+ multiplex assays" refer to an assay wherein at least one antibody against a first biomarker plus (A+) at least one second biomarker are detected and/or measured in the same sample from the same reaction step. In other words, as used herein, "multiplex assay" is used to indicate that the antibody or antibodies and another biomarker, such as an antigen, are detected and/or measured in the same sample from the same reaction step. For example, an "autoAb+TA multiplex assay" which is an autoAb+biomarker multiplex assay refers to an assay wherein at least one autoantibody against a first antigen and at least one second antigen are detected and/or measured in the same sample from the same reaction step. With respect to "multiplex assays", the "same reaction step" means that all the capture reagents are contacted with the sample at once. A+ multiplex assays of the present invention encompass autoAb+biomarker multiplex assays, A+ antigen multiplex assays, autoAb+TA multiplex assays, and the like. An A+ multiplex assay of the present invention may be a MAP based assay.

According to the A+ multiplex assays of the present invention, the capture reagents are selected such that a given capture reagent is not also the biomarker being detected, i.e. a capture antibody is not an antibody to be detected in a sample and a capture antigen is not an antigen to be detected in the sample. Additionally, according to the A+ multiplex assays of the present invention, the detectable label does not specifically bind the unbound capture reagents.

In some embodiments, the capture reagents of the A+ biomarker assays, including A+ multiplex assays, of the present invention are selected so as to minimize cross-reactivity. For example, the epitopes are preferably selected such that an antibody specific for one does not exhibit cross reactivity for another. The epitopes may be further modified using methods known in the art to ensure no cross reactivity with homologous fragments, which could lead to false positive results. For example, sequence analysis can be conducted to identify unique sequences in a given epitope and remove unnecessary amino acid residues that are homologous with other gene products. The modified peptide may be screened using methods known in the art to ensure no loss of binding to its corresponding antibody. Similarly, the antibodies used as the capture reagents for the antigens are preferably selected such that a given antibody does not specifically bind more than one antigen which would likely be in a given test sample, or result in non-specific binding. Other methods known in the art may be used to optimize A+ antigen assays of the present invention.

Further immunoassays using serum samples from 124 healthy subjects, 121 subjects having BPH and 131 subjects suffering from biopsy-confirmed prostate cancer were conducted. The results are as follows:

Table 3 shows the mean value, median value, and SD of MFI values as determined by conventional PSA tests available in the art.

TABLE 3

| | | Dilutions | | | | | | | | |
|---|---|---|---|---|---|---|---|---|---|---|
| | | 1:10 | | | 1:20 | | | 1:50 | | |
| cancer | N | mean | med | SD | mean | med | SD | mean | med | SD |
| No | 121 | −0.20 | −0.34 | 0.80 | −0.10 | −0.24 | 0.80 | −0.04 | −0.18 | 0.80 |
| Yes | 131 | 0.91 | 0.41 | 2.02 | 1.03 | 0.51 | 2.02 | 1.12 | 0.58 | 2.03 |

| cancer | N | mean | med | SD |
|---|---|---|---|---|
| Mean of three dilutions | | | | |
| No | 121 | −0.12 | −0.25 | 0.80 |
| Yes | 131 | 1.02 | 0.50 | 2.02 |
| max of three dilutions | | | | |
| No | 121 | −0.04 | −0.18 | 0.80 |
| Yes | 131 | 1.12 | 0.58 | 2.03 |

As set forth in Table 3, serum samples from patients were diluted at 1/10, 1/20, and 1/50. The diluted serum samples were measured according to the autoAb+PSA assay described herein. An MFI against each peptide was obtained and divided with the MFI from a control peptide, such as a beta-galactosidase peptide. The relative ratio of MFI for each peptide was then obtained. Base on the relative ratios, the mean, median, and SD were calculated. The "NO" cancer category was from 121 BPH/prostatitis patients, while the "YES" category was from the 131 cancer patients. Both categories were normalized with 124 healthy donors. A normalized MFI ratio was defined as (MFI ratio of a patient−mean MFI ratio of healthy donors)/(SD of MFI ratio of healthy donors). These values are not meant to indicate cancer or not, but were used to evaluate and ensure that they contribute to the final autoAb+PSA assay. The final combined autoAb+PSA index was built on top of these values using logistic regression as described above.

Table 4 shows the mean value, median value, and SD of MFI values for PSA levels determined using the autoAb+PSA assay as described herein.

TABLE 4

| | | Dilutions | | | | | | | | |
|---|---|---|---|---|---|---|---|---|---|---|
| | | 1:10 | | | 1:20 | | | 1:50 | | |
| cancer | N | mean | med | SD | mean | med | SD | mean | med | SD |
| No | 121 | −0.39 | −0.34 | 0.80 | −0.42 | −0.24 | 0.80 | −0.46 | −0.18 | 0.80 |
| Yes | 131 | 0.57 | 0.14 | 1.76 | 0.56 | 0.11 | 1.74 | 0.53 | 0.07 | 1.72 |

| cancer | N | mean | med | SD |
|---|---|---|---|---|
| Mean of three dilutions | | | | |
| No | 121 | −0.42 | −0.54 | 0.69 |
| Yes | 131 | 0.55 | 0.10 | 1.74 |
| max of three dilutions | | | | |
| No | 121 | −0.39 | −0.51 | 0.70 |
| Yes | 131 | 0.59 | 0.14 | 1.75 |

As above for Table 3, serum samples from patients were diluted at 1/10, 1/20, and 1/50. The diluted serum samples were measured according to the autoAb+PSA assay described herein. An MFI against each peptide was obtained and divided with the MFI from a control peptide, such as a beta-galactosidase peptide. The relative ratio of MFI for each peptide was then obtained. Base on the relative ratios, the mean, median, and SD were calculated. The "NO" cancer category was from 121 BPH/prostatitis patients, while the "YES" category was from the 131 cancer patients. Both categories were normalized with 124 healthy donors. A normalized MFI ratio was defined as (MFI ratio of a patient−mean MFI ratio of healthy donors)/(SD of MFI ratio of healthy donors). These values are not meant to indicate cancer or not, but were used to evaluate and ensure that they contribute to the final autoAb+PSA assay. The final combined autoAb+PSA index was built on top of these values using logistic regression as described above.

Figure 5:
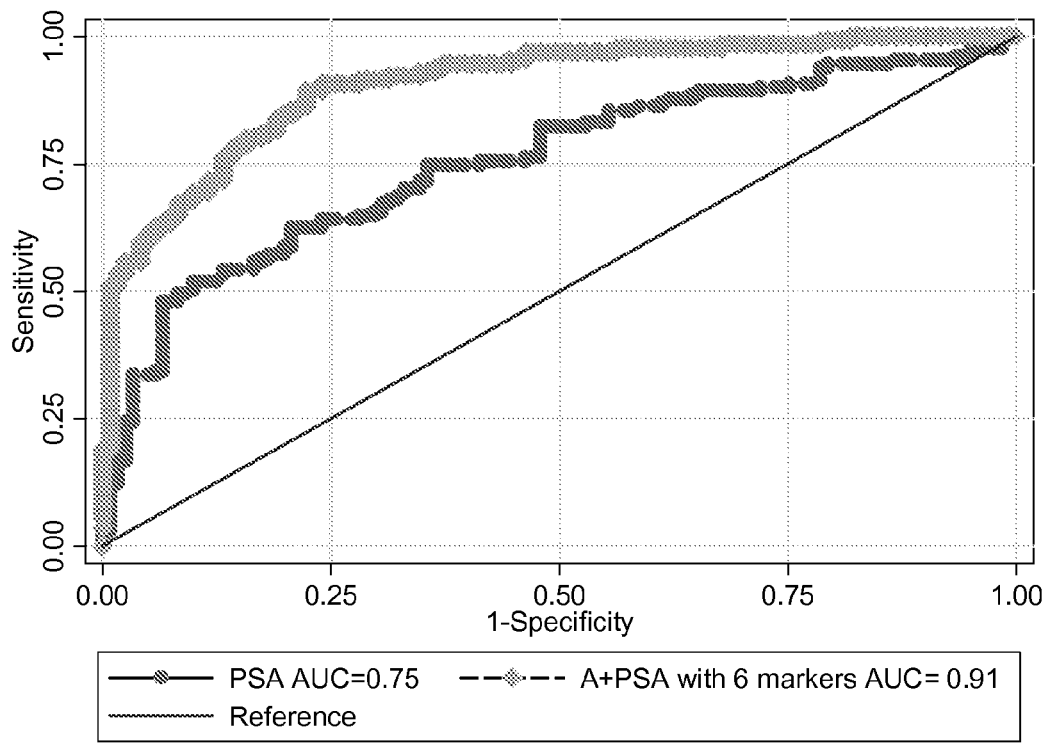
FIG. 5 shows the ROC curves from the PSA and autoAb+ PSA assays of 252 patients (131 with prostate cancer and 121 with BPH) at minimal dilution. PSA levels and autoantibodies were measured in accordance with the autoAb+PSA multiplex assay as described herein.
Figure 6:
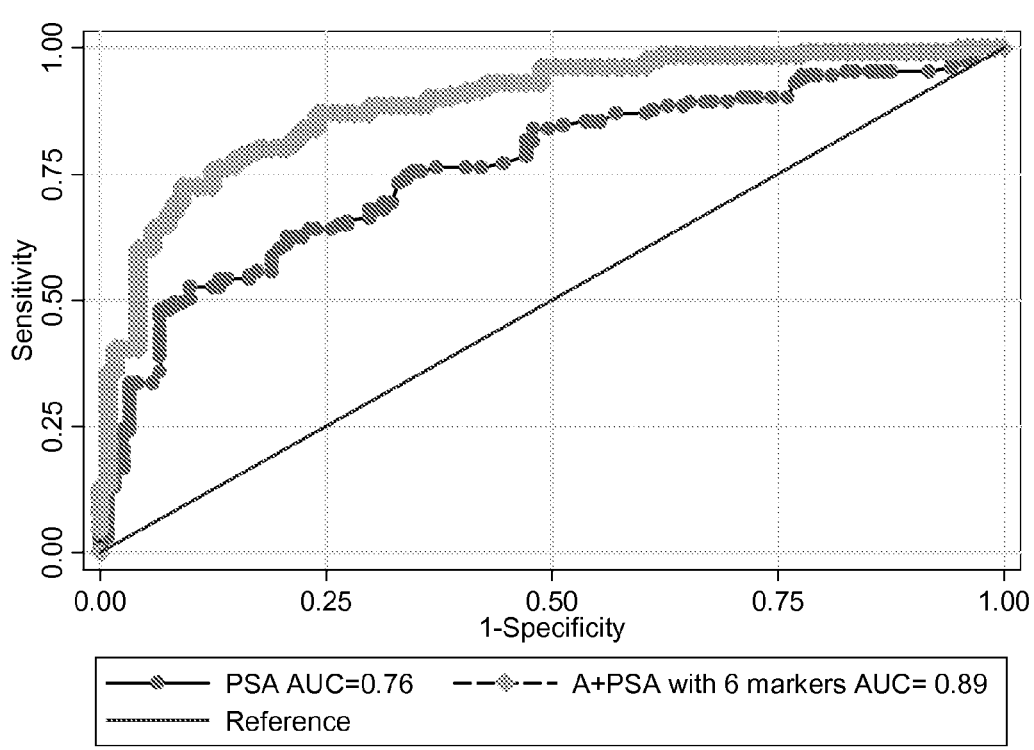
FIG. 6 shows the ROC curves from the PSA and autoAb+ PSA assays of 252 patients (131 with prostate cancer and 121 with BPH) at maximum dilution. PSA levels and autoantibodies were measured in accordance with the autoAb+PSA multiplex assay as described herein.

Table 5 shows the MFI ratios of the autoantibodies against each of the 6 epitopes for mean and SD after normalization:

FIG. 5 shows the ROC curves for mean dilutions and FIG. 6 shows the ROC curves for the max dilutions. As evidenced by the data in these tables, the autoAb+PSA multiplex assay according to the present invention exhibits increased sensitivity, specificity, accuracy and AUC values over PSA alone.

Thus, a MAP based A+ biomarker multiplex assay may be used to determine whether a subject should be classified as healthy (does not have prostate cancer), having BPH or having prostate cancer based on a serum sample obtained from the subject.

For example, patient X is subjected to a MAP based autoAb+PSA multiplex assay to detect autoantibodies against n PCAA(s) and PSA. MFI ratios from n PCAA are calculated as $MFI_1$, $MFI_2$, $MFI_3$, ... $MFI_n$. The probability (p) of patient X having prostate cancer is calculated as $\text{Log}(p/1-p) = \beta_0 + \beta_1 \times MFI_1 + \beta_2 \times MFI_2 + \beta_3 \times MFI_3 \ldots \beta_n \times MFI_n$, where n is the number of PCAAs and βn is the linear coefficient for each of the n PCAA(s) which are determined or were previously determined from a given population group such as described herein for 121 BPH/prostatitis patients and 131 prostate cancer patients. Where p is 0.5 or more, then patient X is designated as having prostate cancer or likely to have prostate cancer.

TABLE 5

| cancer | Dilution | ESO | XAGE | SSX | AM | P90 | LE |
|---|---|---|---|---|---|---|---|
| No (N = 121) | 1:10 | 1.61 (2.86) | 1.04 (1.41) | 0.57 (2.18) | 0.95 (1.94) | 0.76 (2.52) | 0.32 (1.81) |
|  | 1:20 | 1.72 (2.89) | 1.05 (1.43) | 0.64 (2.19) | 1.05 (1.92) | 0.71 (2.48) | 0.50 (1.82) |
|  | 1:50 | 1.69 (2.80) | 1.11 (1.39) | 0.50 (1.89) | 1.07 (1.76) | 0.69 (2.01) | 0.64 (1.65) |
| Yes (N = 131) | 1:10 | 8.51 (32.45) | 4.11 (12.53) | 3.57 (5.48) | 5.65 (28.24) | 3.17 (6.88) | 4.93 (10.58) |
|  | 1:20 | 8.66 (32.74) | 4.18 (12.57) | 3.74 (5.52) | 5.66 (28.05) | 3.29 (6.84) | 5.12 (10.64) |
|  | 1:50 | 8.45 (31.49) | 4.16 (12.13) | 3.24 (4.76) | 5.31 (25.69) | 2.79 (5.50) | 4.78 (9.65) |

| cancer | N | ESO | XAGE | SSX | AM | P90 | LE |
|---|---|---|---|---|---|---|---|
| Mean (SD) of 6 normalized markers from mean of three dilutions | | | | | | | |
| No | 121 | 1.67 (2.85) | 1.07 (1.41) | 0.57 (2.09) | 1.02 (1.88) | 0.72 (2.34) | 0.48 (1.76) |
| Yes | 131 | 8.54 (32.23) | 4.15 (12.41) | 3.51 (5.25) | 5.54 (27.33) | 3.08 (6.41) | 4.94 (10.29) |
| Mean (SD) of 6 normalized markers from the max of three dilution | | | | | | | |
| No | 121 | 1.76 (2.87) | 1.13 (1.40) | 0.68 (2.17) | 1.13 (1.86) | 0.92 (2.43) | 0.67 (1.74) |
| Yes | 131 | 8.75 (32.72) | 4.26 (12.55) | 3.77 (5.50) | 5.78 (28.22) | 3.38 (6.81) | 5.18 (10.62) |

Table 6 compares the sensitivity, specificity, accuracy and AUC for each of the methods.

TABLE 6

| Variables | | Sensitivity | Specificity | Accuracy | AUC | P value |
|---|---|---|---|---|---|---|
| PSA alone: | 1:10 | 63% (82/131) | 77% (93/121) | 69% | 0.75 | |
|  | 1:20 | 63% (82/131) | 77% (93/121) | 69% | 0.75 | |
|  | 1:50 | 64% (84/131) | 77% (93/121) | 70% | 0.76 | |
|  | Mean | 63% (82/131) | 77% (93/121) | 69% | 0.75 | |
|  | Max Dilut. | 64% (84/131) | 77% (93/121) | 70% | 0.76 | |
| A+ PSA: | 1:10 | 75% (98/131) | 82% (99/121) | 78% | 0.86 | A+ PSA vs |
|  | 1:20 | 74% (97/131) | 83% (100/121) | 78% | 0.867 | PSA alone: |
|  | 1:50 | 73% (96/131) | 83% (100/121) | 78% | 0.8695 | P < 0.0001 |
|  | Mean | 80% (106/131) | 81% (99/121) | 81.35% | 0.9058 | in all 4 |
|  | Max Dilut. | 76% (100/131) | 85% (103/121) | 80.56% | 0.8890 | parameters |

Applications

The A+ biomarker assays of the present invention may be used for a variety of research and clinical purposes.

For example, the A+ biomarker assays may be used to create profiles of combinations of various antibodies, including autoantibodies, and antigens (A+ biomarker profiles) for given population groups, e.g. population groups based on age, sex, ethnicity, medical history, geographical location, external factors (e.g. drug, alcohol and smoking habits, pollution, etc.), and the like. These A+ biomarker profiles may be used to further improve the diagnostic power of a given A+ biomarker assay for a given disease for a given subject belonging to a given population group.

A plurality of A+ biomarker profiles of a given population group may be taken over a period of time and before and after certain events, e.g. medical treatments, to give an A+ biomarker profile trend. These A+ biomarker profile trends may be used for 1) early detection, 2) diagnosis, 3) prognosis, 4) treatment planning, and 5) prediction of recurrence of a given disease for a subject belonging to the given population group.

For example, for a given disease, infection or disorder (i.e. given affliction), a subject's A+ biomarker profile may be compared to A+ biomarker profiles (or one standardized or generalized A+ biomarker profile) typical of those having the given affliction (i.e. disease profile) and/or healthy subjects (i.e. healthy profile). If the subject's A+ biomarker profile is similar to or consistent with the disease profile, then the subject is diagnosed as having the given affliction. Alternatively, the subject may be designated or categorized as likely to have or be at risk for the given affliction such that follow-up testing, additional tests, and/or treatments may be planned and conducted. Thus, the A+ biomarker assays of the present invention need not definitively indicate that a subject is at risk for a given affliction or in fact has the given affliction. Instead, the A+ biomarker assays of the present invention may be used to designate a subject as one in need of further testing (e.g. periodic future assays for monitoring, tissue biopsy for confirmation, etc.) and/or treatment (e.g. determine whether one treatment method is preferred over another in view of given biomarkers detected, monitor whether a treatment is having an effect, etc).

Although the A+ biomarker assays exemplified herein relate to PSA and prostate cancer, the A+ biomarker assays of the present invention are not so limited. The A+ biomarker assays of the present invention can be applied to other cancers and diseases including autoimmune diseases and infectious diseases.

In particular, a variety of different cancers may result in autoantibodies which specifically bind the same tumor antigens. For example, prostate cancer, liver cancer, lung cancer, ovarian cancer, breast cancer, and various epithelial cancers all result in autoantibodies which specifically bind NY-ESO-1, XAGE-1b, and SSX-4. Consequently, the autoAb+PSA multiplex assay exemplified herein may be readily modified for assaying a cancer other than prostate cancer by selecting an antibody that is specific for a TA other than PSA as the capture reagent for detecting the TA in a sample. For example, for assaying breast and lung cancers, an antibody which specifically recognizes an CEA may be used as a capture reagent.

Alternatively, the panel of capture reagents may comprise a plurality of epitopes of tumor antigens which are shared by a plurality of cancers and a plurality of antibodies which each specifically bind a TA specific for a given cancer in order to provide a general A+ biomarker assay that can be used to diagnose a subject as suffering from a particular type of cancer and/or rule out other types of cancer. For example, the panel of capture reagents for a general cancer A+ biomarker assay according to the present invention may comprise epitopes of TAs which are shared among a variety of different cancers and antibodies which specifically bind PSA and/or AMACR for prostate cancer, CEA for lung cancer and breast cancer, AFP (alpha fetal protein) for liver cancer, CA125 for ovarian cancer, Her2/neu and/or CA15-3 for various stages of breast cancer, thyroglobulin for thyroid cancer, bladder tumor antigen for urothelial cell carcinoma, CA19.9 for pancreatic cancer, and aspartyl(asparaginyl)beta-hydroxylase (HAAH) for lung cancer. In some embodiments, the panel of capture reagents may further comprise one or more epitopes of TAs which are distinct for specific types of cancer.

The A+ biomarker assays of the present invention may be applied to determining or designating one as having a given infection or autoimmune disease. For example, for determining an infection by virus X, one can measure antibodies against several antigenic epitopes from virus X, e.g. antigen A1, A2, A3, . . . (which could be from different subtypes of virus X, for example, subjects from a given geographical area or ethnicity may have more antibodies against A2, or those infected through a particular route may have antibodies against A5, etc.). At the same time, there is a known biomarker, B for patients who are more prone to infection by virus X. This B biomarker could be a specific HLA subtype, a co-receptor for X infection, a cytokine or chemokine, and the like. The final index could be a combination of measuring antibodies against A1,A2,A3, . . . +B. The combined index can be drawn similarly to the autoAb+PSA assay as exemplified herein to determine the probability of an infection, the prognosis of the infection, and the like. Similarly, the probability of an autoimmune disease including inflammation, the prognosis and the like can be determined according to the A+ biomarker assay according to the present invention.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method of diagnosing or designating a subject as having or likely to have prostate cancer, which comprises
detecting the presence, absence, or amount of at least one autoantibody which specifically binds an epitope of a prostate cancer associated antigen in a sample from the subject said epitope is selected from the group consisting of: AMACR:341-371, p62:156-184, p90:796-827, LEDGFp75:313-345, HIP-1:150-180, and HIP-1:338-375, and detecting the presence, absence, or amount of prostate specific antigen in the sample from the subject,
assigning the presence, absence, or amount of the at least one autoantibody a first weighted value,
assigning the presence, absence, or amount of the prostate specific antigen a second weighted value,
calculating an index value from the first weighted value and the second weighted value, and
(a) diagnosing or designating the subject as having or likely to have prostate cancer based on the index value; and/or
(b) diagnosing or designating the subject as having or likely to have prostate cancer with a probability (p) calculated as $\text{Log}(p/1-p)=\beta 0+\beta_1 \times \text{MFI}_1+\beta_2 \times \text{MFI}_2+\beta_3 \times \text{MFI}_3 \ldots \beta_n \times \text{MFI}_n$, where n is the number of epitopes of prostate cancer associated antigens and $\beta$ is the linear coefficient for each epitope.

2. The method according to claim 1, wherein the detecting steps are conducted in a single reaction step whereby both a first capture reagent for the at least one autoantibody and a second capture reagent for prostate specific antigen are together contacted with the sample.

3. The method of claim 2, wherein the at least one autoantibody is a plurality of autoantibodies.

4. The method according to claim 2, which further comprises detecting the presence, absence, or amount of at least one additional autoantibody which specifically binds an additional epitope selected from the group consisting of: SSX2,4:110-139, NY-ESO-1:1-40, XAGE-1b:1-25, and XAGE-1b:57-87.

5. The method according to claim 3, wherein said plurality of autoantibodies further include one or more additional autoantibodies that specifically bind NY-ESO-1:1-40, XAGE-1b:1-25, XAGE-1b:57-87, or a combination thereof.

6. The method according to claim 5, wherein the one or more additional autoantibodies further include an autoantibody that specifically binds SSX2,4:110-139.

7. The method according to claim 6, wherein the autoantibodies and the additional autoantibodies specifically bind AMACR:341-371, p90:796-827, LEDGFp75:313-345, SSX2,4:110-139, NY-ESO-1:1-40, XAGE-1b:1-25, and XAGE-1b:57-87.

8. The method of claim 2, wherein the first weighted value is based the prevalence of the at least one autoantibody in control subjects suffering from prostate cancer.

9. The method according to claim 2, wherein the first weighted value is assigned 0 for the absence of the autoantibody and 1 for the presence of the autoantibody; and the second weighted value is assigned 0 for a normal amount of the prostate specific antigen, 1 for an abnormally high amount of the prostate specific antigen, or a number between 0 and 1 for an amount of the prostate specific antigen which is between the normal amount and the abnormally high amount.

10. The method of according to claim 2, wherein the subject is diagnosed or designated as having prostate cancer or likely to have prostate cancer where the index value exceeds a given cut-off value.

11. A method of diagnosing or designating a subject as having or likely to have prostate cancer, which comprises
detecting the presence, absence, or amount of autoantibodies against all of the following epitopes: AMACR:341-371, p90:796-827, LEDGFp75:313-345, SSX2,4:110-139, NY-ESO-1:1-40, and XAGE-1b:1-25, in a sample from the subject, and detecting the presence, absence, or amount of prostate specific antigen in a sample from the subject, said detecting steps are performed using a mixture consisting of the following epitopes: AMACR:341-371, p90:796-827, LEDGFp75:313-345, SSX2,4:110-139, NY-ESO-1:1-40, and XAGE-1b:1-25, and an antibody that specifically binds prostate specific antigen, whereby the epitopes and the antibody are contacted with the sample at the same time in the same reaction step by contacting the mixture with the sample,
assigning the presence, absence, or amount of the at least one autoantibody a first weighted value,
assigning the presence, absence, or amount of the prostate specific antigen a second weighted value,
calculating an index value from the first weighted value and the second weighted value, and
(a) diagnosing or designating the subject as having or likely to have prostate cancer based on the index value; and/or
(b) diagnosing or designating the subject as having or likely to have prostate cancer with a probability (p) calculated as $\text{Log}(p/1-p)=\beta 0+\beta_1 \times \text{MFI}_1+\beta_2 \times \text{MFI}_2+\beta_3 \times \text{MFI}_3 \ldots \beta_n \times \text{MFI}_n$, where n is the number of epitopes of prostate cancer associated antigens and $\beta$ is the linear coefficient for each epitope.

12. The method of claim 2, wherein the second weighted value is based on the amount of the prostate specific antigen detected.

13. The method of claim 2, wherein the first weighted value is based on the prevalence of the at least one autoantibody in control subjects suffering from prostate cancer and the second weighted value is based on the amount of the prostate specific antigen detected.

* * * * *

SEQUENCE LISTING

<160> NUMBER OF SEQ ID NOS: 11

<210> SEQ ID NO 1
<211> LENGTH: 31
<212> TYPE: PRT
<213> ORGANISM: Homo sapiens

<400> SEQUENCE: 1

Lys Arg Asp Pro Phe Ile Gly Glu His Thr Glu Glu Ile Leu Glu Glu
1               5                   10                  15

Phe Gly Phe Ser Arg Glu Glu Ile Tyr Gln Leu Asn Ser Asp Lys
            20                  25                  30

<210> SEQ ID NO 2
<211> LENGTH: 32
<212> TYPE: PRT
<213> ORGANISM: Homo sapiens

<400> SEQUENCE: 2

Asp Arg Glu His Lys Leu Ala Asn Leu His Gln Lys Thr Lys Val Gln
1               5                   10                  15

Glu Glu Lys Ile Lys Thr Leu Gln Lys Glu Arg Glu Asp Lys Glu Glu
            20                  25                  30

<210> SEQ ID NO 3
<211> LENGTH: 33
<212> TYPE: PRT
<213> ORGANISM: Homo sapiens

<400> SEQUENCE: 3

Asp Arg Lys Arg Lys Gln Glu Glu Gln Met Glu Thr Glu Gln Gln Asn
1               5                   10                  15

Lys Asp Glu Gly Lys Lys Pro Glu Val Lys Val Glu Lys Lys Arg
            20                  25                  30

Glu

<210> SEQ ID NO 4
<211> LENGTH: 31
<212> TYPE: PRT
<213> ORGANISM: Homo sapiens

<400> SEQUENCE: 4

Met Glu Tyr His Thr Lys Asn Pro Arg Phe Pro Gly Asn Leu Gln Met
1               5                   10                  15

Ser Asp Arg Gln Leu Asp Glu Ala Gly Glu Ser Asp Val Asn Asn
            20                  25                  30

<210> SEQ ID NO 5
<211> LENGTH: 30
<212> TYPE: PRT
<213> ORGANISM: Homo sapiens

<400> SEQUENCE: 5

Lys Ile Met Pro Lys Lys Pro Ala Glu Glu Gly Asn Asp Ser Glu Glu
1               5                   10                  15

Val Pro Glu Ala Ser Gly Pro Gln Asn Asp Gly Lys Glu Leu
            20                  25                  30

<210> SEQ ID NO 6
<211> LENGTH: 25
<212> TYPE: PRT
<213> ORGANISM: Homo sapiens

<400> SEQUENCE: 6

Met Glu Ser Pro Lys Lys Lys Asn Gln Gln Leu Lys Val Gly Ile Leu
1               5                   10                  15

His Leu Gly Ser Arg Gln Lys Lys Ile

<210> SEQ ID NO 7
<211> LENGTH: 40
<212> TYPE: PRT
<213> ORGANISM: Homo sapiens

<400> SEQUENCE: 7

Met Gln Ala Glu Gly Arg Gly Thr Gly Gly Ser Thr Gly Asp Ala Asp
1               5                   10                  15
Gly Pro Gly Gly Pro Gly Ile Pro Asp Gly Pro Gly Gly Asn Ala Gly
            20                  25                  30
Gly Pro Gly Glu Ala Gly Ala Thr
        35                  40

<210> SEQ ID NO 8
<211> LENGTH: 25
<212> TYPE: PRT
<213> ORGANISM: Homo sapiens

<400> SEQUENCE: 8

Gly Val Lys Val Lys Ile Ile Pro Lys Glu Glu His Cys Lys Met Pro
1               5                   10                  15
Glu Ala Gly Glu Glu Gln Pro Gln Val
            20                  25

<210> SEQ ID NO 9
<211> LENGTH: 32
<212> TYPE: PRT
<213> ORGANISM: Homo sapiens

<400> SEQUENCE: 9

Lys Ser Asp Glu Leu Pro Asn Gln Met Ser Met Asp Asp Trp Pro Glu
1               5                   10                  15
Met Lys Lys Lys Phe Ala Asp Val Phe Ala Lys Lys Thr Lys Ala Glu
            20                  25                  30

<210> SEQ ID NO 10
<211> LENGTH: 41
<212> TYPE: PRT
<213> ORGANISM: Homo sapiens

<400> SEQUENCE: 10

Ser Gln Gln Asn Leu Phe Asp Asn Lys Phe Asp Ile Phe Gly Ser
1               5                   10                  15
Ser Phe Ser Ser Asp Pro Phe Asn Phe Asn Ser Gln Asn Gly Val Asn
            20                  25                  30
Lys Asp Glu Lys Asp His Leu Ile Glu
        35                  40

<210> SEQ ID NO 11
<211> LENGTH: 29
<212> TYPE: PRT
<213> ORGANISM: Homo sapiens

<400> SEQUENCE: 11

Asp Glu Glu Val Ser Ser Pro Ser Pro Pro Gln Arg Ala Gln Arg Gly
1               5                   10                  15
Asp His Ser Ser Arg Glu Gln Gly His Ala Pro Gly Gly
            20                  25